United States Patent
Wang et al.

(10) Patent No.: US 11,363,812 B2
(45) Date of Patent: Jun. 21, 2022

(54) CELL FREEZING MEDIUM FOR CLINICAL USE

(71) Applicant: Cellular Biomedicine Group HK Limited, Hong Kong (CN)

(72) Inventors: Fei Wang, Shanghai (CN); Jiaping He, Shanghai (CN); Dijun Zhao, Shanghai (CN); Victor Liu, Shanghai (CN); Dingzhu Yang, Shanghai (CN)

(73) Assignee: CELLULAR BIOMEDICINE GROUP HK LIMITED, Hong Kong (CN)

( * ) Notice: Subject to any disclaimer, the term of this patent is extended or adjusted under 35 U.S.C. 154(b) by 216 days.

(21) Appl. No.: 16/472,962

(22) PCT Filed: Dec. 25, 2017

(86) PCT No.: PCT/CN2017/118381
§ 371 (c)(1),
(2) Date: Jun. 24, 2019

(87) PCT Pub. No.: WO2018/113796
PCT Pub. Date: Jun. 28, 2018

(65) Prior Publication Data
US 2019/0357525 A1    Nov. 28, 2019

(30) Foreign Application Priority Data

Dec. 23, 2016 (CN) .......................... 2016112049018

(51) Int. Cl.
| | | |
|---|---|---|
| *A01N 1/02* | (2006.01) | |
| *C07K 14/765* | (2006.01) | |
| *C12N 5/00* | (2006.01) | |
| *C12N 5/0783* | (2010.01) | |
| *C12N 5/0775* | (2010.01) | |

(52) U.S. Cl.
CPC .......... *A01N 1/0221* (2013.01); *A01N 1/0226* (2013.01); *C07K 14/765* (2013.01); *C12N 5/0037* (2013.01); *C12N 5/0636* (2013.01); *C12N 5/0663* (2013.01); *C12N 2500/16* (2013.01); *C12N 2500/32* (2013.01); *C12N 2500/35* (2013.01); *C12N 2500/38* (2013.01); *C12N 2500/50* (2013.01); *C12N 2500/62* (2013.01)

(58) Field of Classification Search
None
See application file for complete search history.

(56) References Cited

FOREIGN PATENT DOCUMENTS

| CN | 1935989 | A |   | 3/2007 |
|---|---|---|---|---|
| CN | 102948413 | A |   | 3/2013 |
| CN | 103404509 | A |   | 11/2013 |
| CN | 103583511 | A |   | 2/2014 |
| CN | 103783031 | A |   | 5/2014 |
| CN | 104082277 | A |   | 10/2014 |
| CN | 104542578 | A | * | 4/2015 |
| CN | 104542578 | A |   | 4/2015 |
| CN | 105123671 | A | * | 12/2015 |
| CN | 105123671 | A |   | 12/2015 |
| CN | 106234354 | A |   | 12/2016 |

OTHER PUBLICATIONS

Thermofisher Catalog No. 11320-DMEM/F-12 (2015) https://www.thermofisher.com/us/en/home/technical-resources/media-formulation.55.html (Year: 2015).*
Matejtschuk P, Dash CH, Gascoigne EW. Production of human albumin solution: a continually developing colloid. Br J Anaesth. Dec. 2000;85(6):887-95. (Year: 2000).*
Weiner M, Slatko B. Kits and their unique role in molecular biology: a brief retrospective. Biotechniques. Apr. 2008;44(5):701-4. (Year: 2008).*
International Search Report (English and Chinese) and Written Opinion issued in PCT/CN2017/118381, dated Mar. 27, 2018, 11 pages.

* cited by examiner

*Primary Examiner* — Peter Paras, Jr.
*Assistant Examiner* — Austin Jeffries
(74) *Attorney, Agent, or Firm* — Leason Ellis LLP

(57) ABSTRACT

Provided in the present invention is a cell freezing medium for clinical use. In particular, the cell freezing medium of the present invention comprises the following components: (1) human albumin; (2) cryoprotectant: the cryoprotectant comprises a combination of one or more of dimethyl sulfoxide, glycerol, and ethylene glycol; (3) a saline buffer; wherein the salt buffer is a solution containing $Na^+$, $K^+$, $Mg^+$, $Cl^-$, and $CH_3COO^-$ ions; (4) a vitamin; and (5) an amino acid, wherein the human albumin concentration is 1%-20% (w/v). The cell, after long-term cryopreservation with the freezing medium of the present invention, has a high viability, and the cellular efficiency maintains a high uniformity. The grade of purity of the freezing medium of the present invention is the pharmaceutical grade or USP grade; and the freezing medium is safe and reliable for clinical use, and can be used or conventional adherent and suspension cells.

11 Claims, 5 Drawing Sheets

CELL FREEZING MEDIUM FOR CLINICAL USE

FIELD OF INVENTION

The present invention relates to the field of biotechnology and, in particular, to the cell freezing medium for the long-term storage and clinical use of stem cells.

BACKGROUND OF THE INVENTION

After the cell culture reaches the required or targeted amount, the cultured cells need to be collected and stored. However, neither room temperature condition or 4° C. can be sufficient for long-term preservation of cells, thus requiring cryopreservation of cells, which would involve the use of cryopreservation solutions.

At present, conventional cryopreservation solutions are composed of serum or animal-derived proteins, or common chemical reagents that do not meet clinical use. On one hand, such cryopreservation solutions have a poor effect on cell viability or potency. On the other hand, these cryopreservation solutions are difficult to meet the standards for clinical use since the ingredients thereof can hardly be unified.

In summary, there is still a lack of cell cryopreservation solution which is of uniform quality and suitable for clinical use in the field.

SUMMARY OF INVENTION

It is an object of the present invention to provide a cell cryopreservation solution of uniform quality and suitable for clinical use.

In the first aspect of the present invention, a cell cryopreservation solution for clinical use is provided, wherein it comprises the following ingredients:
  (1) human albumin;
  (2) cryoprotectant, which includes one or more of dimethyl sulfoxide, glycerin, and ethylene glycol, or the combinations thereof;
  (3) a salt buffer, which is a solution containing $Na^+$, $K^+$, $Mg^+$, $Cl^-$, and $CH_3COO^-$ ions;
  (4) vitamins; and
  (5) amino acids;
wherein, the concentration of human albumin is 1%-20% (w/v).

In a preferred embodiment, the concentration of human albumin is 3-15% (w/v), more preferably 4-12% (w/v).

In a preferred embodiment, the concentration of the cryoprotectant is 0.4-2.2 mol/L.

In a preferred embodiment, the cryoprotectant is selected from the group consisting of dimethyl sulfoxide, glycerin, ethylene glycol, or the combinations thereof.

In a preferred embodiment, the cryoprotectant is dimethyl sulfoxide.

In a preferred embodiment, the cell cryopreservation solution comprises one or more characteristics selected from the group consisting of:
  The concentration of $Na^+$ ions is 0.1-0.2 mol/L;
  The concentration of $K^+$ ions is 5-10 mmol/L;
  The concentration of $Mg^{2+}$ ions is 1.5-5 mmol/L;
  The concentration of ions is 0.1-0.3 mol/L;
  The concentration of $CH3COO^-$ ions is 40-60 mmol/L.

In a preferred embodiment, the salt buffer is a multiple electrolytes injection.

In a preferred embodiment, the concentration of vitamin is 50 mmol/L-150 mmol/L; and/or the amino acid concentration is 0.1 mol/L-0.5 mol/L.

In a preferred embodiment, the human albumin is selected from the group consisting of plasma extracted human albumin, recombinant human albumin, or the combinations thereof.

In a preferred embodiment, the vitamin is selected from the group consisting of vitamin A, vitamin B, vitamin C, vitamin D, vitamin E, vitamin K, or the combinations thereof.

In a preferred embodiment, the vitamin is selected from the group consisting of vitamin A, vitamin B, vitamin C, vitamin E, or the combinations thereof.

In a preferred embodiment, the vitamin is selected from the group consisting of vitamin C, vitamin E, or the combinations thereof.

In a preferred embodiment, the amino acid is selected from the group consisting of glycine, alanine, valine, leucine, isoleucine, phenylalanine, proline, tryptophan, serine, tyrosine, cysteine, methionine, asparagine, glutamine, threonine, aspartic acid, glutamic acid, lysine, arginine, histidine, or the combinations thereof preferably lysine, tryptophan, phenylalanine, methionine, threonine, isoleucine, leucine, valine, or the combinations thereof.

In a preferred embodiment, the amino acid is selected from the group consisting of glycine, arginine, leucine, phenylalanine, or the combinations thereof.

In the second aspect of the present invention, a cell mixture is provided, wherein the mixture comprises:
  cells, and
  cell cryopreservation solution according to the first aspect of the invention;
  preferably, the cells are Car-T cells, mesenchymal stem cells, or the combinations thereof.

In a preferred embodiment, the cell mixture is a mixture of cells after cryopreservation.

In a preferred embodiment, the cell mixture is used for long-term preservation of cells and/or establishment of cell banks.

In the third aspect of the present invention, a method for cryopreservation of cells is provided, wherein it comprises:
  (i) mixing the cells to be cryopreserved with the cell cryopreservation solution according to the first aspect of the invention, thereby obtaining a cell mixture;
  (ii) cooling the cell mixture obtained in the step (i) and storing in liquid nitrogen.

In another preferred embodiment, the cells to be cryopreserved in the step (i) are prepared by the following steps:
  (i-1) providing a living cell and calculating the viability and cell density;
  (i-2) centrifuging the cells of the step (i-1), removing the supernatant, and bounce off the cell pellet.

In a preferred embodiment, the step (ii) is cooled to −80 degrees by program gradient cooling method.

In the fourth aspect of the invention, a kit for cryopreservation of cells is provided, which comprises the cell cryopreservation solution according to the first aspect of the invention.

It is to be understood that, in the present invention, the various technical features of the present invention and the various technical features specifically described hereinafter (as in the embodiments) may be combined with each other to constitute a new or preferred technical solution, which are not specifically described one by one because of the limitation of context.

DESCRIPTION OF FIGURES OF THE INVENTION

Figure 4:
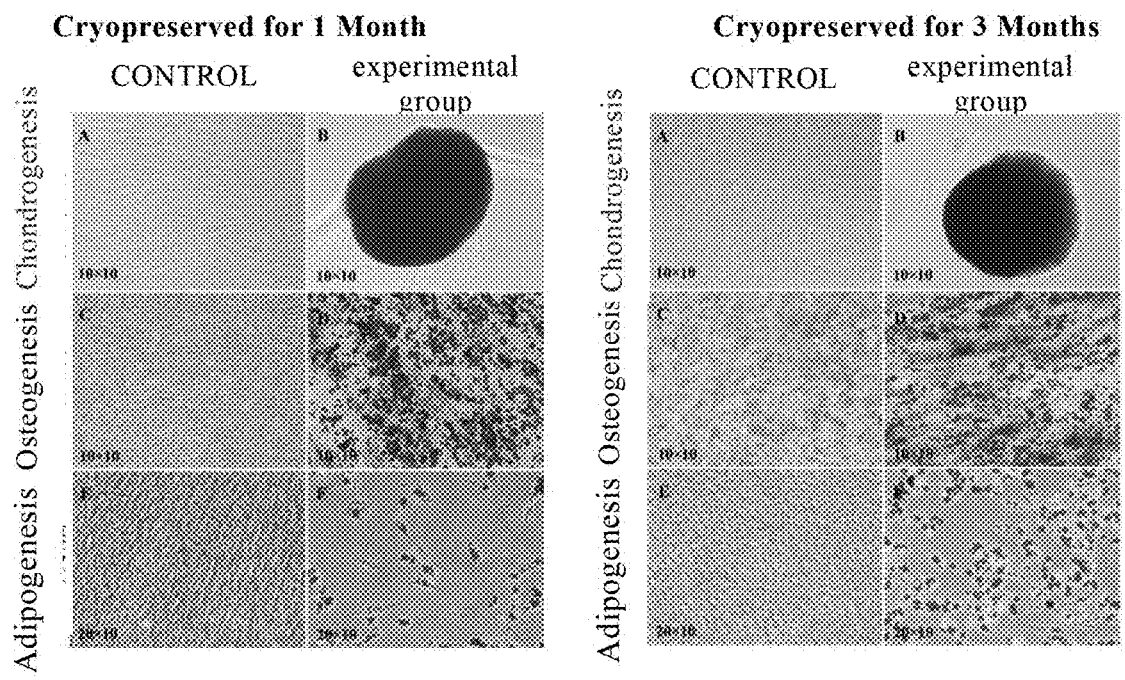

FIG. 4 shows the comparison diagram of differentiation between mesenchymal stem cells cryopreserved for 1 month and 3 months and fresh cells before cryopreservation in example 2.

Figure 5:
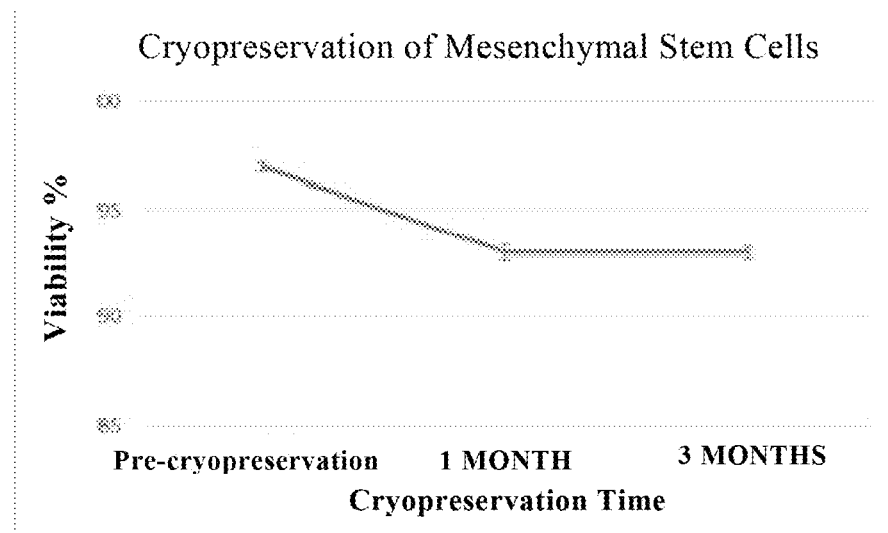

FIG. 5 shows the relationship between the viability of the mesenchymal stem cells and the cryopreservation time of example 3.

Figure 6:
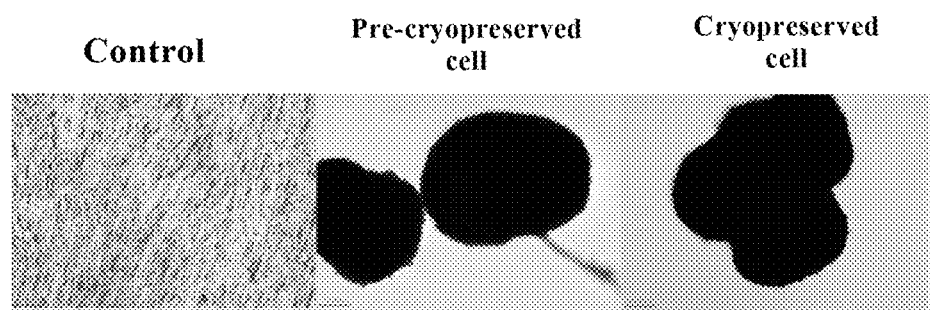

FIG. 6 shows the comparison of chondrogenic differentiation of the mesenchymal stem cells of example 3.

Figure 7:
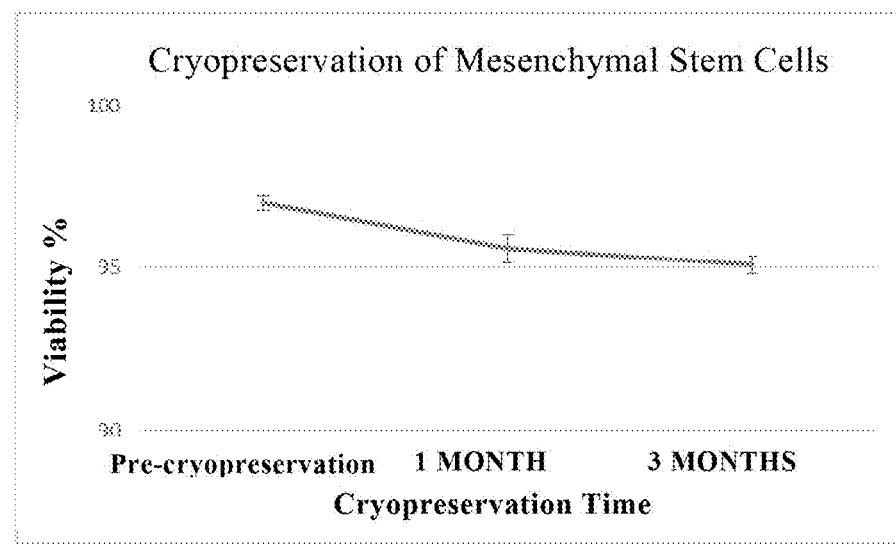

FIG. 7 shows the relationship between the viability of the mesenchymal stem cells and the cryopreservation time of Example 4.

Figure 8:
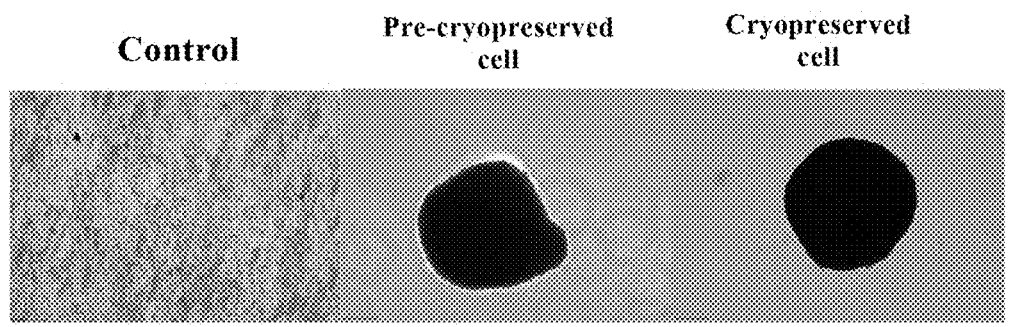

FIG. 8 shows the comparison of chondrogenic differentiation of the mesenchymal stem cells of example 4.

Figure 9:
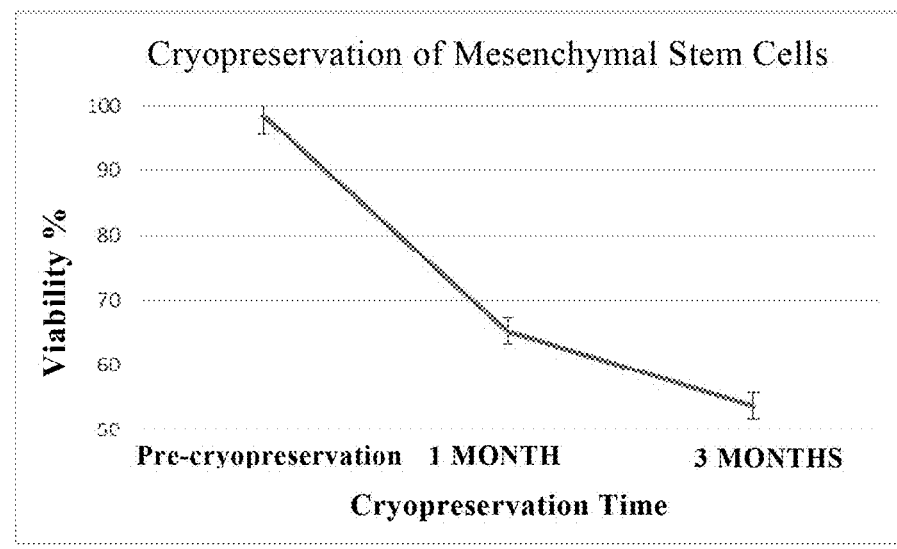

FIG. 9 shows the relationship between the viability of the mesenchymal stem cells and the cryopreservation time of comparative example 1.

Figure 10:
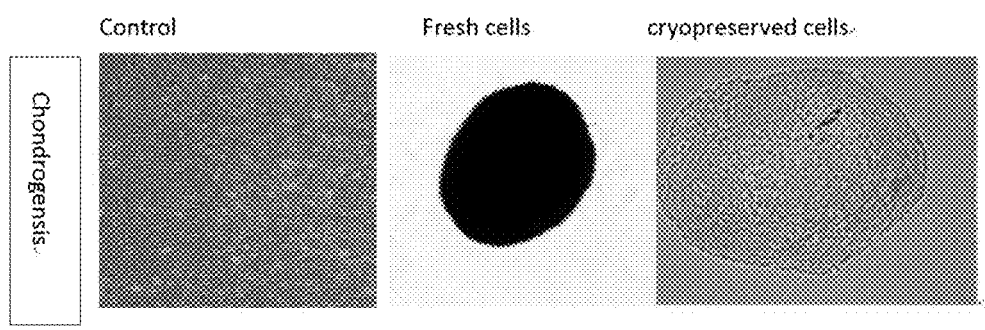

FIG. 10 shows the comparison of chondrogenic differentiation of the mesenchymal stem cells of comparative example 1.

DETAILED DESCRIPTION OF THE INVENTION

Through comprehensive and intensive research, the inventor has discovered for the first time that when using a cryopreservation solution containing human albumin, vitamins, and amino acids for the preservation of cells such as mesenchymal stem cells, the good viability and expression ability of cells can be preserved even after long-term storage. The present invention is accomplished based on the discovery.

Terms

Human Albumin

As used herein, the term "human albumin" includes plasma extracted human albumin and recombinant human albumin. The "human albumin" as used in the specific examples and comparative examples of the present invention refers to plasma extracted human albumin, while "recombinant human albumin" refers to genetic recombinant human albumin.

Mesenchymal Stem Cell

As used herein, "mesenchymal stem cells" refers to pluripotent stem cells derived from the early developmental mesoderm with high self-renewal ability and multi-directional differentiation potential which widely present in various tissues of the whole body, and can be cultured and expanded in vitro so as to differentiate into nerve cells, osteoblasts, muscle cells, fat cells, etc. under the control of specific conditions.

CAR-T Cell

As used herein, "CAR-T cell", which is a chimeric antigen receptor T cell, is produced by in vitro coupling an antigen binding portion of an antibody capable of recognizing a certain tumor antigen to an intracellular portion of a CD3-ζ chain or FcεRIγ to form a chimeric protein, and transfect the patient's T cells by gene transduction to express a chimeric antigen receptor (CAR).

Cell Cryopreservation

Cell cryopreservation technology is an important means of biological preservation of species. If cells are directly frozen without any condition, water in the inner and outer cell environment forms ice crystals, resulting in mechanical damage, electrolyte increase, osmotic pressure change, dehydration, pH change, protein denaturation, etc., and in extreme cases causes cell death. The freezing point will drop when protecting agent is added into the culture medium. Under slow freezing conditions, the intracellular water would permeate out from the cells before freezing, thus reducing the formation of ice crystals when stored at low temperatures.

The cryopreservation solution is the most important part for cryopreservation. The traditional cryopreservation solution contains animal serum, mainly fetal calf serum and/or bovine calf serum. Serum is a sort of extremely complex mixtures which are produced by removing fibrin from plasma. Some of the constituents of serum are still unclear. Moreover, the composition and contents of the serum would vary from sex, age, physiological condition and nutritional conditions of the animal donor. Serum comprises various plasma proteins, peptides, fats, carbohydrates, hormones, and inorganics, etc.

Recovery of Cells

As used herein, the term "recovery of cells" refers to the process in which the cells are re-activated from dormant state. Generally, rapid recovery, a procedure known by the skilled in the art, is used in the recovery of cells, which comprises quickly shifting the freezing tube from liquid nitrogen into warm water bath of which the temperature is preferably 37° C.-40° C.; stirring in variable interval to speed up unfreezing; sterilizing the freezing tube after the cells are completely unfrozen; washing and re-suspending the unfrozen cells, transferring the cells into cell culture flask and cultivating in $CO_2$ incubator; and determining the survival rate and viability of cells.

Cell Cryopreservation Method

In a specific embodiment of the invention, the cryopreservation and resuscitation steps of Car-T cells are as follows:

1. Take a bag of Car-T cells cultured in suspension for 14 days, calculate the viability and cell density, and collect the viable cell volume $4\times10^8$ for centrifugation;

2. After centrifugation, remove the supernatant, bounce off the cell pellet, and slowly add 20 mL of the frozen solution;

3. Mix and dispense the mixture into two 20 mL frozen storage bags, and put them into the program cooling instrument to cool to −80 degrees;

4. The cells were stored in liquid nitrogen, and samples were taken at 1 week and 6 weeks for detection and analysis of cell viability and functional expression.

In a specific embodiment of the invention, the cryopreservation and resuscitation steps of mesenchymal stem cells are as follows:

1. The mesenchymal stem cells adherent cultured in the plate are taken, and the degree of fusion is observed to be 80% to 90%. The cells are collected by trypsinization, and the viability and cell density were calculated. The viable cells were collected by centrifugation at an amount of $4\times10^7$.

2. After centrifugation, remove the supernatant, bounce off the cell pellet, and slowly add 3 mL of the cryopreservation solution;

3. Mix and dispense into two 2 mL frozen storage bags, and put them into the program cooling instrument to cool down to −80 degrees;

4. Store in liquid nitrogen, and samples are taken after 1 month and 3 months for the analysis of cell viability and differentiation ability.

Cell Cryopreservation

The maintain environment of cells should be an isotonic solution. Salt buffers such as physiological saline or a compound electrolyte injection can maintain cell osmotic pressure. During cryopreservation, the water in cells need to be replaced with cryoprotectant so as to prevent the formation of ice crystals in the cryopreservation process damaging the organelles. Meanwhile, the metabolism of the cells after recovered from cryopreservation needs to consume vitamins and amino acids.

The present inventor has unexpectedly discovered that the cell cryopreservation solution which is prepared by adding salt buffer solution, human albumin, vitamins, amino acids and a cryoprotectant into physiological saline is able to cryopreserve cells for a long time and can maintain a high survival rate and strong functional expression and differentiation ability of recovery cells.

The cell cryopreservation solution of the present invention comprises the following components:
(1) salt buffer;
(2) human albumin;
(3) vitamins;
(4) amino acids;
(5) cryoprotectant.

The salt buffer includes, but is not limited to: one or more of physiological saline, compound electrolyte injection, phosphate buffer, and combinations thereof. The cryoprotectant includes, but is not limited to, one or more of dimethyl sulfoxide, glycerin, ethylene glycol, and combinations thereof.

The cell cryopreservation solution of the invention can be used for:
(a) preserving the cells;
(b) establishing a cell bank;
(c) maintaining cell viability.

Cell Mixture

The cell mixture of the invention comprises the following components:
(a) cells;
(b) cell cryopreservation solution, including the following components:
(1) salt buffer;
(2) human albumin;
(3) vitamins;
(4) amino acids;
(5) cryoprotectant.

The salt buffer includes, but is not limited to, one or more of physiological saline, multiple electrolytes injection, and phosphate buffer, or the combinations thereof. The cryoprotectant includes, but is not limited to, one or more of dimethyl sulfoxide, glycerin, and ethylene glycol, or the combinations thereof.

The Main Advantages of the Cell Cryopreservation Solution of the Present Invention Include:
(1) Cells can be cryopreserved for a long time while still keeping high survival rate after recovery;
(2) Cells recovered after cryopreservation can keep good functional expression and differentiation ability.

The present invention is further illustrated below with reference to the specific embodiments. It should be understood that these examples are only to illustrate the invention but not to limit the scope of the invention. The experimental methods in the following examples with no specific conditions are usually produced according to the conditions described in the conventional conditions, for example, Sambrook et al., Molecular Cloning: Laboratory Manual (New York: Cold Spring Harbor Laboratory Press, 1989), or according to the manufacturing conditions. The conditions recommended by the manufacturer. Unless otherwise stated, percentages and parts are by weight and parts by weight.

Example 1

The formulation of the cryopreservation solution used in this embodiment is as follows:

| No. | Reagent | Formulation plan |
|-----|---------|------------------|
| 1 | $Na^+$ | 140 mmol/L |
| 2 | $K^+$ | 6 mmol/L |
| 3 | $Mg^{2+}$ | 2 mmol/L |
| 4 | $Cl^-$ | 110 mmol/L |
| 5 | $CH_3COO^-$ | 40 mmol/L |
| 6 | Human albumin | 8% (W/V) |
| 7 | Dimethyl sulfoxide | 1.4 mol/L |
| 8 | Vitamin C | 50 mmol/L |
| 9 | Glycine | 0.1 mol/L |
| 10 | Arginine | 0.1 mol/L |

The specific freezing and recovery steps were as follows:

1. A bag of Car-T cells cultured in suspension for 14 days was taken to calculate the viability and cell density, and $4 \times 10^8$ viable cells was collected.

2. The supernatant was removed by centrifugation. The cell pellet was bounced off, and 20 ml of cryopreservation solution was slowly added.

3. After well mixed, the mixture was added to two 20 ml frozen storage bags, and put into a program cooling instrument to cool down to −80 degree.

4. The mixture was stored in liquid nitrogen, and sampled after 1 week and 6 weeks respectively.

Figure 1:
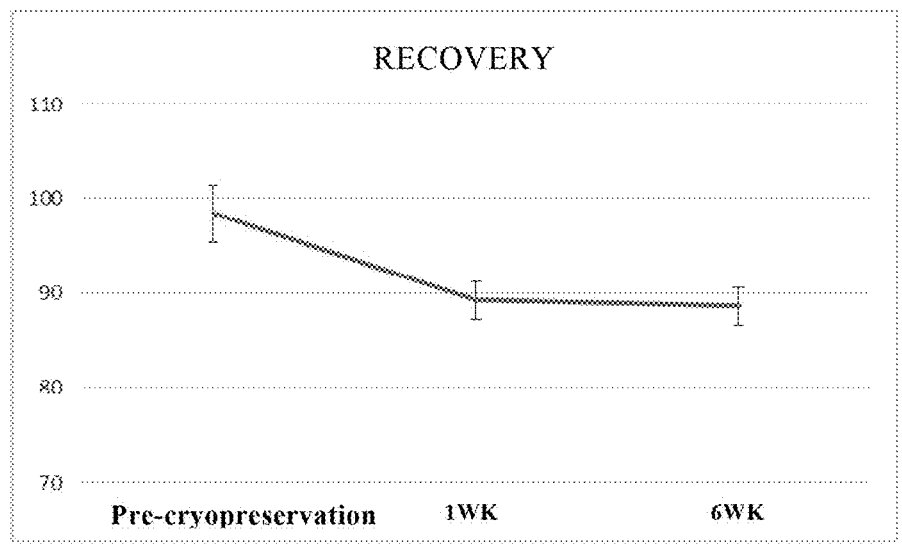
FIG. 1 shows the relationship between Car-T cell viability and cryopreservation time in example 1.

The results of Car-T cell viability after cryopreservation are shown in FIG. 1. According to the experimental statistics, the decrease of viability was within 10% after 1 to 6 weeks of cryopreservation, and the results of 1 week and 6 weeks were stable, which indicates that the effect of the frozen solution was in line with the demand.

Figure 2:
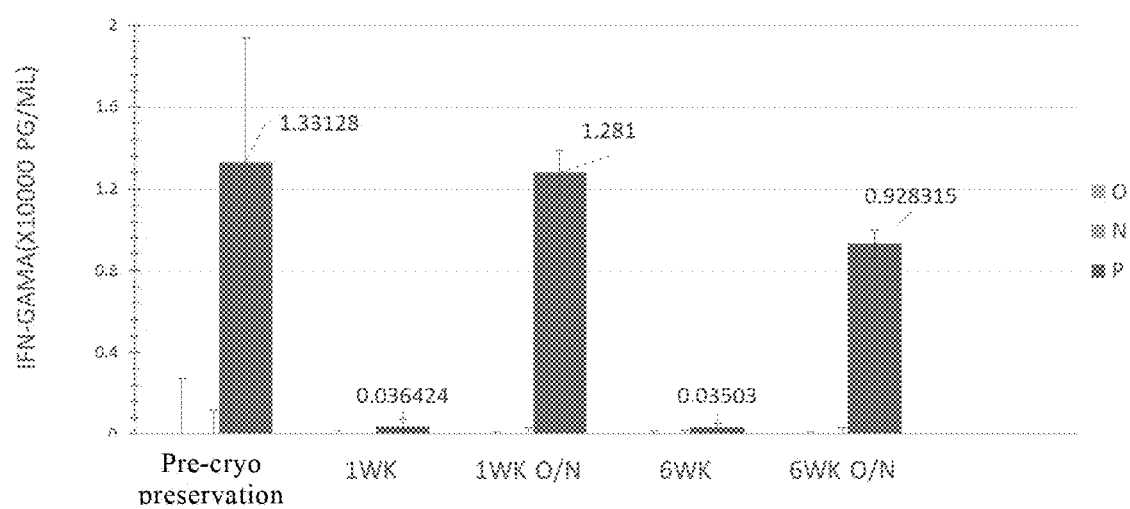
FIG. 2 shows the relationship between Car-T function expression ability and cryopreservation time in example 1.

The test results of the relationship between Car-T functional expression ability and cryopreservation time are shown in FIG. 2. In the figure, O\N\P groups respectively indicate:

O: CarT cells only
N: CarT cells+CD19 negative tumor cells
P: CarT cells+CD19 positive tumor cells It can be seen from the figure that the O\N group (control group and negative group) were almost without any expression, and the P group has still shown strong expression ability, so only the P group can be detected. The results shows that the cells still had strong functional expression ability after 1 to 6 weeks of cryopreservation, and the decrease was not significant compared with that before cryopreservation.

Example 2

The formulation of the cryopreservation solution used in this embodiment is as follows:

| No. | Reagent | Formulation plan |
| --- | --- | --- |
| 1 | $Na^+$ | 140 mmol/L |
| 2 | $K^+$ | 6 mmol/L |
| 3 | $Mg^{2+}$ | 2 mmol/L |
| 4 | $Cl^-$ | 110 mmol/L |
| 5 | $CH_3COO^-$ | 40 mmol/L |
| 6 | Human albumin | 5% (W/V) |
| 7 | Dimethyl sulfoxide | 0.7 mol/L |
| 8 | Vitamin C | 60 mmol/L |
| 9 | Glycine | 0.2 mol/L |
| 10 | Arginine | 0.2 mol/L |

The specific freezing and recovery steps were as follows:

1. Several plates of mesenchymal stem cells adherent cultured were taken, and the degree of fusion was observed to be 80% to 90%. The cells were collected by trypsinization, and the viability and cell density were calculated. The viable cells were collected by centrifugation at an amount of $4 \times 10^7$.

2. The supernatant was removed after centrifugation, and cell pellet was bounced off, and 3 ml cryopreservation solution was slowly added;

3. The mixture was mixed and packed into two 2 ml frozen storage bags, and put into the program cooling instrument to cool down to −80 degree;

4. Stored in liquid nitrogen and sampled after 1 month and 3 months respectively.

Figure 3:
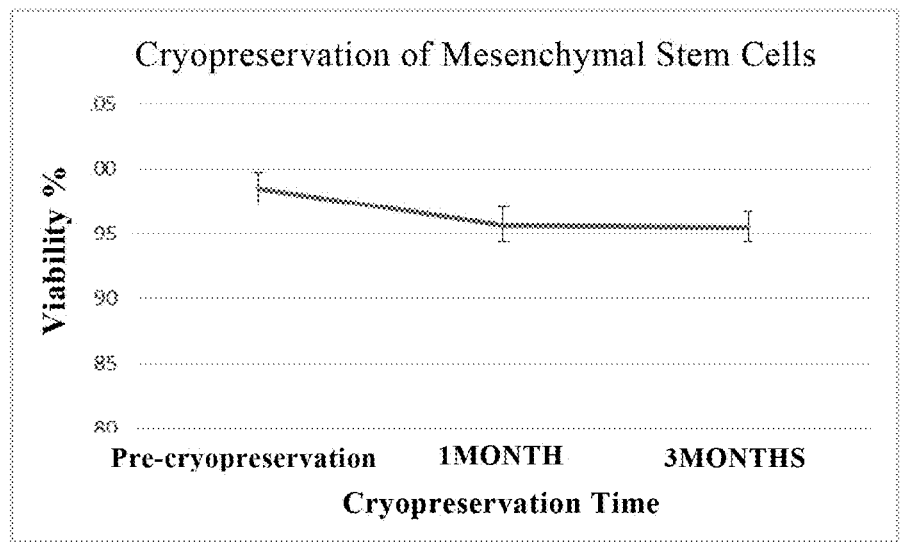
FIG. 3 shows the relationship between the viability of the mesenchymal stem cells and the cryopreservation time of example 2.

The relationship between the viability of mesenchymal stem cells and cryopreservation time was shown in FIG. 3. The results showed that after 1 to 3 months of cryopreservation, the decrease of cell viability was within 5%, which reached up to 95% or more, thus complying with the demand of clinical use.

The results of the test for differentiation potency of mesenchymal stem cells after cryopreservation were shown in FIG. 4. The results has shown that in the differentiation experiment, after 1 month and 3 months of cryopreservation, the adipogenic, osteogenic and chondrogenic ability of the cells were not affected when compared with fresh pre-cryopreservation cells.

Example 3

The formulation of the cryopreservation solution used in this embodiment is as follows:

| No. | Reagent | Formulation plan |
| --- | --- | --- |
| 1 | $Na^+$ | 140 mmol/L |
| 2 | $K^+$ | 6 mmol/L |
| 3 | $Mg^{2+}$ | 2 mmol/L |
| 4 | $Cl^-$ | 110 mmol/L |
| 5 | $CH_3COO^-$ | 40 mmol/L |
| 6 | Recombinant human albumin | 5% (W/V) |
| 7 | Dimethyl sulfoxide | 0.7 mol/L |
| 8 | Vitamin C | 60 mmol/L |
| 9 | Glycine | 0.2 mol/L |
| 10 | Arginine | 0.2 mol/L |

The specific freezing and recovery steps were as follows:

1. Several plates of mesenchymal stem cells adherent cultured were taken, and the degree of fusion was observed to be 80% to 90%. The cells were collected by trypsinization, and the viability and cell density were calculated. The viable cells were collected by centrifugation at an amount of $4 \times 10^7$.

2. The supernatant was removed after centrifugation, and cell pellet was bounced off, and 3 ml cryopreservation solution was slowly added;

3. The mixture was mixed and packed into two 2 ml frozen storage bags, and put into the program cooling instrument to cool down to −80 degree;

4. Stored in liquid nitrogen and sampled after 1 month and 3 months respectively.

The viability analysis was shown in FIG. 5. The results show that after 1 to 3 months of, the decrease of cell viability was within 7%, which reached uo to 93%, thus complying with the demand of clinical use.

The results of the differentiation ability test were shown in FIG. 6. The results has shown that in the differentiation experiment, after 1 month of cryopreservation with recombinant human albumin cryopreservation solution, the differentiation ability is basically the same as that of the fresh pre-cryopreservation cells.

Example 4

The formulation of the cryopreservation solution used in this embodiment was as follows:

| No. | Reagent | Formulation plan |
| --- | --- | --- |
| 1 | $Na^+$ | 140 mmol/L |
| 2 | $K^+$ | 6 mmol/L |
| 3 | $Mg^{2+}$ | 2 mmol/L |
| 4 | $Cl^-$ | 110 mmol/L |
| 5 | $CH_3COO^-$ | 40 mmol/L |
| 6 | Human albumin | 5% (W/V) |
| 7 | Dimethyl sulfoxide | 0.7 mol/L |
| 8 | Vitamin E | 60 mmol/L |
| 9 | Leucine | 0.1 mol/L |
| 10 | Phenylalanine | 0.2 mol/L |

The specific freezing and recovery steps are as follows:

1. Several plates of mesenchymal stem cells adherent cultured were taken, and the degree of fusion was observed to be 80% to 90%. The cells were collected by trypsinization, and the viability and cell density were calculated. The viable cells were collected by centrifugation at an amount of $4 \times 10^7$.

2. The supernatant was removed after centrifugation, and cell pellet was bounced off, and 3 ml cryopreservation solution was slowly added;

3. The mixture was mixed and packed into two 2 ml frozen storage bags, and put into the program cooling instrument to cool down to −80 degree;

4. Stored in liquid nitrogen and sampled after 1 month and 3 months respectively.

The relationship between the viability of cryopreserved mesenchymal stem cells and cryopreservation time was shown in FIG. 7. The results showed that after 1 to 3 months of cryopreservation, the decrease of cell viability was within 5%, which reached up to 95%, thus complying with the demand of clinical use.

The results of the test for differentiation potency were shown in FIG. 8. It can be seen from the figure that in the differentiation experiment, after 1 month of cryopreservation with other vitamins and amino acid cryopreservation solution, the differentiation ability of the cells was basically the same as that of the fresh pre-cryopreservation cells.

Comparative Example 1

The formulation of the preservation solution used in this embodiment is as follows:

| No. | Reagent | Formulation plan |
|---|---|---|
| 1 | $Na^+$ | 140 mmol/L |
| 2 | $K^+$ | 6 mmol/L |
| 3 | $Mg^{2+}$ | 2 mmol/L |
| 4 | $Cl^-$ | 110 mmol/L |
| 5 | $CH_3COO^-$ | 40 mmol/L |
| 6 | Human albumin | 40% (W/V) |
| 7 | Dimethyl sulfoxide | 5 mol/L |

The specific freezing and recovery steps were as follows:

1. Several plates of mesenchymal stem cells adherent cultured were taken, and the degree of fusion was observed to be 80% to 90%. The cells were collected by trypsinization, and the viability and cell density were calculated. The viable cells were collected by centrifugation at an amount of $4\times10^7$.

2. The supernatant was removed after centrifugation, and cell pellet was bounced off, and 3 ml cryopreservation solution was slowly added;

3. The mixture was mixed and packed into two 2 ml frozen storage bags, and put into the program cooling instrument to cool down to −80 degree;

4. Stored in liquid nitrogen and sampled after 1 month and 3 months respectively.

The viability analysis results of the mesenchymal stem cells after cryopreserved with the cryopreservation solution described in the present comparative example are shown in FIG. 9. It can be seen from the figure that when the concentration of human albumin and dimethyl sulfoxide was too high, the cells appear to decrease drastically after cryopreserved for 1 to 3 months, especially within 1 month, which indicates that the cryopreservation solution failed to protect the cell viability during cryopreservation.

The results of the differentiation ability test were shown in FIG. 10. As can be seen from the figure, in the differentiation experiment, after cryopreserved for 1 month with the high dimethyl sulfoxide cryopreservation solution, the chondrogenic ability was significantly decreased compared with the fresh pre-cryopreservation cells.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

The invention claimed is:

1. A cell cryopreservation solution for long-term storage of a mammalian stem cell, comprising:
   a. a human albumin;
   b. a cryoprotectant comprising one or more of dimethyl sulfoxide, glycerin, and ethylene glycol;
   c. a salt buffer comprising $Na^+$, $K^+$, $Mg^{2+}$, $Cl^-$, and $CH_3COO^-$ ions;
   d. a vitamin; and
   e. amino acids;
   wherein the human albumin is present at a concentration of 1%-20% weight by volume (w/v),
   the amino acids consist of a combination of glycine and arginine or a combination of leucine and phenylalanine, and
   the amino acids are independently present at a concentration of 0.1 mol/L-0.5 mol/L.

2. The cell cryopreservation solution of claim 1, wherein the cryoprotectant is present at a concentration of 0.4 mol/L-2.2 mol/L.

3. The cell cryopreservation solution of claim 1, wherein concentrations of $Na^+$, $K^+$, $Mg^{2+}$, $Cl^-$, and $CH_3COO^-$ in the salt buffer are one or more concentrations selected from the group consisting of:
   a concentration of the $Na^+$ ions being 0.1-0.2 mol/L;
   a concentration of the $K^+$ ions being 5-10 mmol/L;
   a concentration of the $Mg^{2+}$ ions being 1.5-5 mmol/L;
   a concentration of the $Cl^-$ ions being 0.1-0.3 mol/L; and
   a concentration of the $CH_3COO^-$ ions being 40-60 mmol/L.

4. The cell cryopreservation solution of claim 1, wherein the vitamin is present at a concentration of 50 mmol/L-150 mmol/L.

5. The cell cryopreservation solution of claim 1, wherein the human albumin is selected from the group consisting of a plasma extracted human albumin, a recombinant human albumin, and a combination thereof.

6. The cell cryopreservation solution of claim 1, wherein the vitamin is selected from the group consisting of vitamin A, vitamin B, vitamin C, vitamin E, vitamin K, and combinations thereof.

7. The cell cryopreservation solution of claim 1, wherein the vitamin is vitamin C or vitamin E.

8. A mammalian cell mixture, comprising:
   a mammalian cell and the cell cryopreservation solution of claim 1.

9. A method for cryopreservation of a mammalian cell, comprising:
   (i) mixing the mammalian cell to be cryopreserved with the cell cryopreservation solution of claim 1, thereby obtaining a mammalian cell mixture;
   (ii) cooling the mammalian cell mixture obtained in step (i) and storing the mammalian cell mixture in liquid nitrogen.

10. A kit for cell cryopreservation, comprising the cell cryopreservation solution of claim 1.

11. The mammalian cell mixture of claim 8, wherein the mammalian cell is a mesenchymal stem cell or a CAR-T cell.

* * * * *